United States Patent
Meldrum et al.

(10) Patent No.: US 9,597,026 B2
(45) Date of Patent: Mar. 21, 2017

(54) ENDOSCOPE FOR ANALYTE CONSUMPTION RATE DETERMINATION WITH SINGLE CELL RESOLUTION FOR IN VIVO APPLICATIONS

(71) Applicants: Deirdre Meldrum, Phoenix, AZ (US); Laimonas Kelbauskas, Gilbert, AZ (US); Jeff Houkal, Los Angeles, CA (US); Roger Johnson, Phoenix, AZ (US); Yanqing Tian, Tempe, AZ (US); Cody Youngbull, Tempe, AZ (US)

(72) Inventors: Deirdre Meldrum, Phoenix, AZ (US); Laimonas Kelbauskas, Gilbert, AZ (US); Jeff Houkal, Los Angeles, CA (US); Roger Johnson, Phoenix, AZ (US); Yanqing Tian, Tempe, AZ (US); Cody Youngbull, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 303 days.

(21) Appl. No.: 14/538,557

(22) Filed: Nov. 11, 2014

(65) Prior Publication Data
US 2015/0133757 A1     May 14, 2015

Related U.S. Application Data

(60) Provisional application No. 61/903,610, filed on Nov. 13, 2013.

(51) Int. Cl.
  *A61B 5/1455* (2006.01)
  *A61B 5/1459* (2006.01)
  *A61B 5/00* (2006.01)

(52) U.S. Cl.
  CPC ......... *A61B 5/1459* (2013.01); *A61B 5/1455* (2013.01); *A61B 5/6847* (2013.01)

(58) Field of Classification Search
  CPC .............. A61B 5/1455; A61B 5/14551; A61B 5/14556; A61B 5/1459; A61B 5/6846; A61B 5/6847; A61B 1/07
  See application file for complete search history.

(56) References Cited

U.S. PATENT DOCUMENTS

| | | | | |
|---|---|---|---|---|
| 4,718,417 A | * | 1/1988 | Kittrell | .............. A61B 1/00183 600/342 |
| 5,000,901 A | * | 3/1991 | Iyer | ..................... A61B 5/1459 600/342 |

(Continued)

FOREIGN PATENT DOCUMENTS

WO     2007127512 A2     8/2007

OTHER PUBLICATIONS

Bosch et al., (2007). "Recent Development in Optical Fiber Biosensors." Sensors 7: 797-859.

(Continued)

*Primary Examiner* — Eric Winakur
(74) *Attorney, Agent, or Firm* — Quarles & Brady LLP; Gavin J. Milczarek-Desai

(57) ABSTRACT

Novel methods and devices including modified endoscopes that employ fiber optic technology and multiple extrinsic optical sensors for enablement of simultaneous determination of change rates of biological analytes in vivo with single-cell resolution. The devices employ dynamic oscillatory actuation to determine the gradient of analytes of interest along one or multiple directions with respect to the cell. The change rate or flux of the analyte of interest can be easily determined by applying the first Fick's law that relates the flux with the concentration gradient. The dual operation mode of the device markedly increases measurement sensitivity and accuracy.

11 Claims, 3 Drawing Sheets

(56) References Cited

U.S. PATENT DOCUMENTS

| | | | | |
|---|---|---|---|---|
| 5,119,463 | A * | 6/1992 | Vurek | A61B 5/1459 600/325 |
| 5,495,850 | A * | 3/1996 | Zuckerman | A61B 5/14555 600/323 |
| 5,596,988 | A * | 1/1997 | Markle | A61B 5/1459 600/353 |
| 7,787,923 | B2 | 8/2010 | Alarcon et al. | |
| 8,460,195 | B2 * | 6/2013 | Courtney | A61B 5/0062 600/459 |

OTHER PUBLICATIONS

Leung et al., (2007). "A Review of Fiber-Optic Biosensors." Sensors and Actuators B 125: 688-703.

Lim, (2003). "Detection of Microorganisms and Toxins with Evanescent Wave Fiber-Optic Biosensors." Proceedings of the IEEE 91(6): 902-907.

Mignani et al., (1996). "Biomedical sensors using optical fibres." Rep. Prog. Phys. 59: 1-28.

Moser et al., (2013). "Pre-Calibrated Biosensors for Single-Use Applications." Chemie Ingenieur Technik 85(1-2): 172-178.

Pantano et al., (1995). "Analytical Applications of Optical Imaging Fibers." Analytical Chemistry 481-487.

Wang et al., (2013). "Fiber-Optic Chemical Sensors and Biosensors." Anal. Chem. 85: 487-508.

\* cited by examiner

ENDOSCOPE FOR ANALYTE CONSUMPTION RATE DETERMINATION WITH SINGLE CELL RESOLUTION FOR IN VIVO APPLICATIONS

CROSS-REFERENCE TO RELATED APPLICATIONS

This application claims the benefit of U.S. provisional Application No. 61/903,610 filed on Nov. 13, 2013, which is incorporated by reference herein in its entirety.

FEDERALLY SPONSORED RESEARCH OR DEVELOPMENT

This invention was made with government support under NIH/NHGRI grant 5P50 HG002360 awarded by the National Institute of Health. The government has certain rights in the invention.

FIELD OF THE INVENTION

The present disclosure relates to a method for simultaneous measurement of change rates of biological analytes in vivo with single cell resolution. The present disclosure also relates to a device including a modified endoscope utilizing fiber optic technology for simultaneous measurement of change rates of biological analytes in vivo with single cell resolution.

BACKGROUND OF THE INVENTION

Determination of consumption/secretion rates with single cell resolution in vivo bears a great potential for delivering detailed insights into early onset and development of various disease states in highly heterogeneous tissues and are of great importance for drug and stimulus response analysis. This information, however, is currently unavailable due to the lack of sensitivity of current technologies. On the one hand, single-cell measurements in vivo are especially challenging due to the close packaging of cells in tissues while on the other hand, analyte concentration changes induced by individual cells are extremely low. It therefore would be advantageous to have methods and devices that would overcome these challenges.

SUMMARY OF THE INVENTION

The present disclosure provides novel methods and devices including a modified endoscope that employs a fiber optic approach and multiple extrinsic optical sensors that enable simultaneous determination of transmembrane fluxes of multiple biological analytes in vivo with single-cell resolution.

In an embodiment, the inventive device employs dynamic oscillatory actuation to determine the gradient of analytes of interest along one or multiple directions with respect to a cell. The change rate or flux of the analyte of interest can be easily determined by applying the first Fick's law that relates the flux with the concentration gradient. The dual operation mode of the device markedly increases measurement sensitivity and accuracy.

In an embodiment, the device can be employed for measurements at a more coarse scale, e.g. scale from tens to hundreds cells to millimeter or centimeter large areas in vivo, by increasing the dimensions of the fiber-coupled sensor. The same dynamic sensing principle (further referred to as Dynamisens) would apply.

Hence, embodiments described herein can be used for a broad variety of purposes in the clinic that benefit from direct monitoring of tissue and cell function in vivo.

These and other aspects of the invention will be apparent upon reference to the following detailed description and figure.

DETAILED DESCRIPTION OF THE INVENTION

Figure 1:
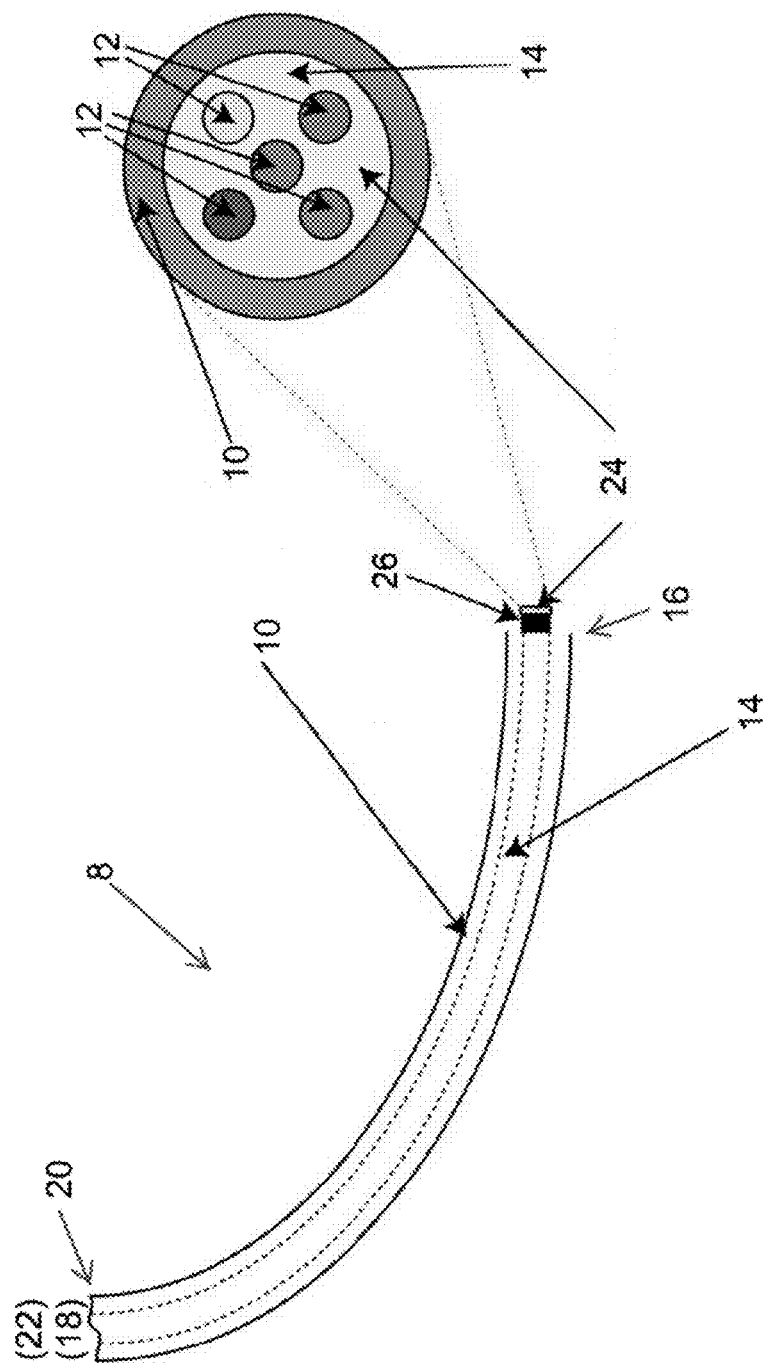
FIG. 1 depicts a conceptual schematic of an endoscope embodiment for in vivo measurements of transmembrane fluxes with single-cell resolution. The illustrated sensors can be sensitive to a number of analytes, such as oxygen, pH, potassium, ATP, glucose, etc.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present embodiments, suitable methods and materials are described below. The materials, methods and examples are illustrative only, and are not intended to be limiting. All publications, patents and other documents mentioned herein are incorporated by reference in their entirety.

The term "a" or "an" may mean more than one of an item.

The terms "and" and "or" may refer to either the conjunctive or disjunctive and mean "and/or".

In one embodiment, a novel device (e.g. a modified endoscope) is disclosed that enables multiparameter measurements of transmembrane fluxes in tissues in vivo with single-cell resolution. For instance, the device enables the simultaneous determination of change rates of biological analytes in vivo with single-cell resolution by employing dynamic oscillatory actuation to determine the gradient of analytes of interest along one or multiple directions with respect to a cell. The change rate or transmembrane flux of the analyte of interest can be easily determined by applying the first Fick's law that relates the flux with the concentration gradient. The dual operation mode of the device markedly increases measurement sensitivity and accuracy.

The device is based on a fiber-optic approach and a combination of multiple extracellular optical sensors that change their properties in response to concentration changes of analytes of interest. Fiber-optic communication is a method of transmitting information from one place to another by sending pulses of light through an optical fiber. The light forms an electromagnetic carrier wave that is modulated to carry information. A light guide, which is a bundle of optical fibers can be used to make a long thin probe that can be inserted into the body cavity by certain prescribed means. This probe forms a main component of the endoscope. For instance, the probe may be covered by a flexible tubing, which may allow for analyte delivery.

The light guide and the tubing of the present invention device are both highly flexible to enable in vivo applications under complex geometrical confinements. The light guide serves as a light delivery medium for the excitation photons to reach the sensor at the distal end as well as sensor emission light delivery medium to the detector at the opposite (proximal) end.

An optical fiber as defined in the art may be a long, thin strand of clear material. Its shape is usually similar to a cylinder. In the center, it has a core. Around the core is a layer called the cladding. The core and cladding are made of different kinds of glass or plastic, so that light travels slower in the core than it does in the cladding. If the light in the core hits the edge of the cladding at a shallow angle, it reflects. Light can travel inside the core and bounce off of the cladding. No light usually escapes until it comes to the end of the fiber. Since the light does not leak out of the fiber much as it travels, the light can go a long distance without a significant attenuation of the signal. Hence, optical fibers are attractive tools for endoscopy.

FIG. 1 illustrates a conceptual schematic of an endoscope device 8 for in vivo measurements of transmembrane fluxes of analytes with single-cell resolution. In the present embodiment, an outer flexible tube 10 includes extrinsic optical sensors (sensing elements) 12 that are attached to the tip of light guide 14 at the distal end 16. These sensors change their emission light parameters in a well-known relation to the analytes that they are intended to measure. The light guide 14 transmits the excitation light radiation emitted by a light source 18 at the proximal end 20 to the sensors 12 at the distal end 16 and further, transports the emission light radiation, modulated by the concentration of the corresponding analytes, from the sensors 12 to a detector 22 at the proximal end 20. A sensor button 24 is also provided at the distal end to regulate the exposure of sensors to corresponding analytes. A piezo actuator 26 that both causes and measures the displacement of the sensors may be present at the distal end. One end of the piezo actuator 26 may be attached to the light guide 14 and the other end may be attached to the sensor button 24.

The optical sensors are highly attractive for endoscopy. First, they are very sensitive. Next, many light signals can be sent over the same optical path (fiber), because light signals at different frequencies do not interfere with one another. Further, they generate a distinct change in optical signal only when the target analyte is present. Finally, optical signals do not require a material medium to travel in. A variety of optical sensing mechanisms exist, including fluorescence, Raman scattering, resonance or other phenomena. The need to measure multiple parameters can be fulfilled by bundling several sensors together wherein the sensors can be based on fluorescence, Raman scattering, resonance or other phenomena.

The working principle of the device exploits the first Fick's law to determine the flux of the analyte by measuring the analyte gradient along one or several directions with regard to a single cell. In addition, to increase the measurement sensitivity, the analyte gradient can be actively controlled by flowing analytes at known concentration and flux. The combination of the external analyte concentration/ gradient control with the oscillatory actuation (motion) of the optode (optical sensor) can significantly increase the measurement sensitivity as compared to measurements with no active modulation of the external analyte concentration.

Figure 2:
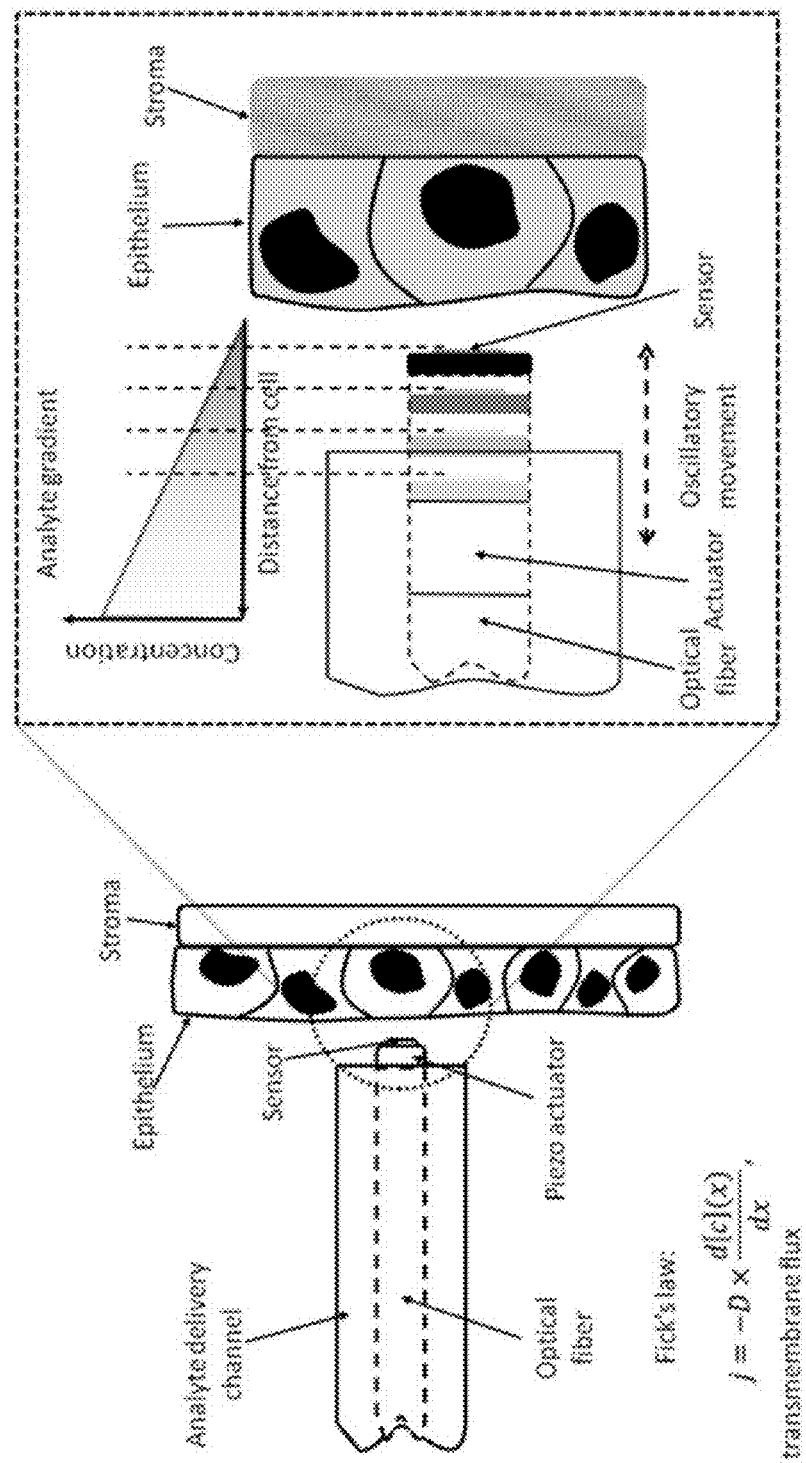
FIG. 2 illustrates a conceptual working principle of the device.

FIG. 2 illustrates a conceptual working principle of the device. The sensor attached to the end of the optical fiber is brought into close vicinity of a cell in tissue. Transmembrane flux of an analyte of interest is measured by incurring oscillatory motion of the sensor along the optical axis of the fiber. Due to an existing concentration gradient, this change in distance between the cell and sensor causes the sensor to be exposed to different analyte concentrations along the movement direction, thereby enabling measurements of the spatial gradient of the analyte.

Figure 3:
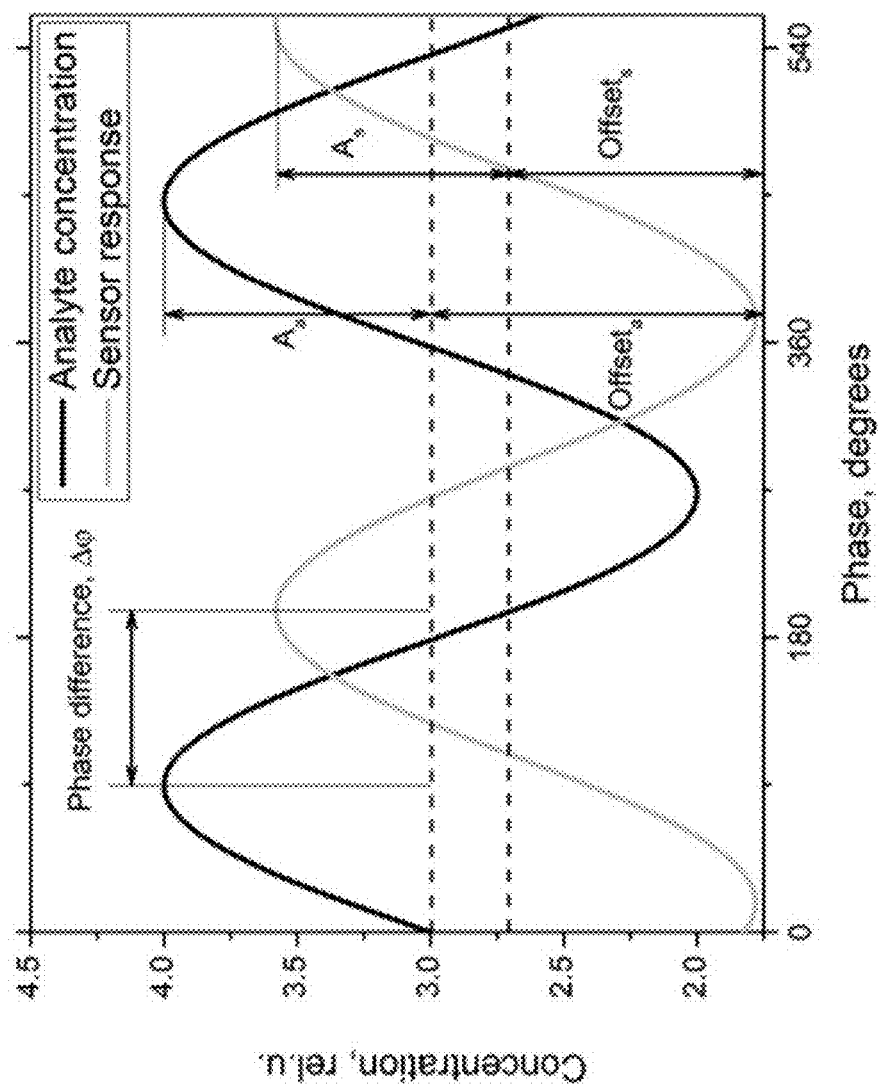
FIG. 3 depicts the change rates of an analyte due to cellular activity, which can be calculated from the displacement of the optode and changes in modulation depth and phase shift of the external analyte flux.

The external flux of the analyte through the flexible tubing is modulated in a sinusoidal or other well-defined pattern and alterations in both its phase and amplitude as a result of cell consumption/production of the analyte as measured by the sensor. The change rates of the analyte due to cellular activity can be calculated from the displacement of the optode and changes in modulation depth and phase shift of the external analyte flux (FIG. 3). The optode displacement is actively controlled by a piezo actuator, which is attached to the light guide on one side and to the sensor button on the other side.

As the sensor button is actuated back and forth with respect to the fiber end, the sensors are exposed to different levels of corresponding analytes and, thus, respond with different emission signal amplitudes. These can be detected by a sensitive detector on the opposite end of the light guide. The gradient can then directly be calculated and the analyte flux can be determined. To increase measurement sensitivity, the sensor actuation can be complemented by an external flow of an analyte modulated in sinusoidal or other patterns can be delivered through the tubing enclosing the light guide in close vicinity of the cell. If, for example, the cell is consuming the analyte, the sinusoidal modulation pattern detected by the corresponding sensor will have lower amplitude and a delayed phase shift. The amplitude and phase alterations combined with the position information of the optode provide a markedly increased sensitivity and accuracy as compared with each one of the approaches.

The device can be equipped with in vivo imaging capability for 3D mapping and characterization of tissue under examination. The device can also be combined with conventional biopsy forceps and used for guiding the collection of biopsy material based on analyte concentration and/or transmembrane flux. The use of the combination of actively controlled sensor actuation with respect to tissue and active analyte flow along with multi-parameter sensing of different analytes of interest is novel. The ability to measure metabolic rates in vivo in single cells is novel. The device can be utilized for a variety of applications in the clinic that require the assessment of tissue health (e.g. metabolic activity and profile, hormone and/or cytokine secretion rates etc.) in vivo.

Further, the single-cell resolution enables measurements of histopathological heterogeneity and holds the potential of detecting early events in disease onset, including carcinogenesis. In combination with other techniques in the clinical practice, such as endoscopy, informed decision making by the clinician can be markedly improved. It can also be used in diagnostics, drug screening, response monitoring and therapeutics.

In addition, the device will be mostly advantageous in clinical settings, while research groups studying tissues could also benefit. For example, one potential and most direct area of use would be in monitoring of progression to esophageal adenocarcinoma in Barrett's esophagus patients for risk stratification. The current status quo of the screening is based on endoscopy and visual assessment of the inner lining of the esophagus. By combining this device with the current standard-of-care, the accuracy and prognostic levels can be increased significantly. Other applications include examination of areas bordering tumors during surgery, examination of mouth cavity for abnormal lesions, skin lesions inspection etc.

The claims are not intended to be limited to the embodiments and examples described herein.

What is claimed is:

1. A modified endoscope utilizing fiber optics for simultaneous measurement of changes in multiple biological analytes in vivo with single cell resolution comprising:
 a proximal end and a distal end, wherein the proximal end is adapted to be placed outside a body and the distal end is adapted to be placed inside the body;
 at least two different optical sensors on the distal end, wherein the sensors respond to concentration changes of different analytes of interest with at least one of different light emission signal amplitudes, emission temporal characteristics, or spectral characteristics;
 a sensor button on the distal end, wherein the sensor button can be actuated back and forth to regulate the exposure of the sensors to the analytes;
 a piezo actuator on the distal end, wherein the actuator is coupled to a light guide on one end, to the sensor button on the other end, and is positioned to control the displacement of the sensors at the distal end;
 a sensitive detector on the proximal end, wherein the detector is configured to detect the emitted light of each of the sensors; and
 a light guide configured to serve as a light delivery medium from a light source to the sensors at the distal end and as a emission light delivery medium from the sensors to the detector at the proximal end.

2. The modified endoscope of claim 1, wherein the light guide is surrounded by a tubing that is flexible and operative for analyte delivery to the distal end.

3. The modified endoscope of claim 2, wherein the flexible tubing and the light guide are configured to enable in vivo applications under complex geometrical confinements.

4. The modified endoscope of claim 2, wherein the endoscope is configured to determine analyte flux by measuring an analyte gradient along one or several directions with regard to a single cell in vivo.

5. The modified endoscope of claim 4, wherein the analyte gradient can be actively controlled by flowing analytes through the flexible tubing at a known concentration and flow rate.

6. The modified endoscope of claim 5, wherein a combination of external analyte concentration with an oscillatory actuation of the optical sensors significantly increases the measurement sensitivity as compared to measurements with no active modulation of the external analyte concentration.

7. The modified endoscope of claim 6, wherein the external flux of the analyte through the flexible tubing is modulated in a sinusoidal or other well-defined pattern such that alterations in both phase and amplitude result from cellular activity.

8. The modified endoscope of claim 7, wherein change rates of the analyte due to cellular activity are calculated from displacement of the optical sensors and changes in modulation depth and phase shift of external analyte flux.

9. The modified endoscope of claim 1, wherein the endoscope is equipped with in vivo imaging capability.

10. The modified endoscope of claim 1, wherein the endoscope is equipped with biopsy material collection capability.

11. A method for simultaneous measurement of changes in multiple biological analytes with single cell resolution in vivo comprising:
 positioning a distal end of a modified endoscope inside the body at a place of interest;
 delivering light through a light guide from a proximal end of the endoscope to at least two optical sensors at the distal end;
 actuating a sensor button at the distal end to expose the sensors to the analytes of interest;
 transmitting a light emission signal amplitude of each of the sensors corresponding to a change in concentration gradient of the analytes; and
 measuring the analytes concentration gradient change transmitted by the sensors with a sensitive detector.

* * * * *